(12) United States Patent
Karle et al.

(10) Patent No.: US 9,597,345 B2
(45) Date of Patent: Mar. 21, 2017

(54) KIT-IN-PARTS FOR CLEANING AND TREATING EARS OF COMPANION ANIMALS

(75) Inventors: Joachim Karle, Ruesselsheim (DE); Reinhard Seffner, Basdahl (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 269 days.

(21) Appl. No.: 13/996,014

(22) PCT Filed: Dec. 21, 2011

(86) PCT No.: PCT/EP2011/073566
§ 371 (c)(1),
(2), (4) Date: Sep. 20, 2013

(87) PCT Pub. No.: WO2012/085068
PCT Pub. Date: Jun. 28, 2012

(65) Prior Publication Data
US 2015/0038441 A1    Feb. 5, 2015

(30) Foreign Application Priority Data

Dec. 23, 2010  (EP) .................................. 101969107

(51) Int. Cl.
| | | |
|---|---|---|
| A61K 31/14 | (2006.01) |
| C07C 211/63 | (2006.01) |
| A61K 31/7048 | (2006.01) |
| A61K 9/00 | (2006.01) |
| A61K 9/08 | (2006.01) |
| A61K 31/573 | (2006.01) |
| A61K 31/575 | (2006.01) |
| A61K 31/7036 | (2006.01) |
| A61K 45/06 | (2006.01) |
| A61K 47/10 | (2006.01) |
| A61K 47/20 | (2006.01) |
| A61K 47/44 | (2006.01) |
| A61K 31/045 | (2006.01) |
| A61K 31/055 | (2006.01) |
| A61K 31/155 | (2006.01) |
| A61K 31/19 | (2006.01) |
| A61K 31/245 | (2006.01) |
| A61K 31/565 | (2006.01) |
| A61K 31/60 | (2006.01) |

(52) U.S. Cl.
CPC ........ *A61K 31/7048* (2013.01); *A61K 9/0046* (2013.01); *A61K 9/08* (2013.01); *A61K 31/045* (2013.01); *A61K 31/055* (2013.01); *A61K 31/14* (2013.01); *A61K 31/155* (2013.01); *A61K 31/19* (2013.01); *A61K 31/245* (2013.01); *A61K 31/565* (2013.01); *A61K 31/573* (2013.01); *A61K 31/575* (2013.01); *A61K 31/60* (2013.01); *A61K 31/7036* (2013.01); *A61K 45/06* (2013.01); *A61K 47/10* (2013.01); *A61K 47/20* (2013.01); *A61K 47/44* (2013.01); *C07C 211/63* (2013.01)

(58) Field of Classification Search
None
See application file for complete search history.

(56) References Cited

U.S. PATENT DOCUMENTS

| 4,025,620 A | * | 5/1977 | Beyer et al. .................. 424/115 |
| 6,793,932 B2 | | 9/2004 | Lopez Cabrera et al. |
| 2003/0068294 A1 | | 4/2003 | Lopez Cabrera et al. |
| 2009/0111780 A1 | * | 4/2009 | Giordano ...................... 514/171 |

FOREIGN PATENT DOCUMENTS

| WO | 2005055921 A2 | 6/2005 |
| WO | 2009023943 A1 | 2/2009 |
| WO | 2012085068 A1 | 6/2012 |

OTHER PUBLICATIONS

Dyer, L. Furze, C. Maddox, C. Sales, R. (2006) Administration of Medicines in Practices in Children's Nursing (2nd Edition), Trigg, E.; Mohammed, T. (eds) Elseive.*
Pappas et al., "Topical Antibiotic Ear Drops: Are They Safe?" J Clin Pract (2006) vol. 9 pp. 1115-1119.*
Cole, "Anatomy and physiology of the canine ear" Veterinary Dermatology (2009) vol. 20 pp. 412-421.*
"Otitis externa in animals". Wikipedia, the free encyclopedia, Mar. 1, 2010, pp. 1-2.
Cabenda et al., "Serous otitis media (S.O.M.) A baceteriological study of the ear canal and the middle ear". International Journal of Pediatric Otorhinolaryngology, vol. 16, 1988, pp. 119-124.
Galle et al., "Ototoxicity of the antiseptic combination chlorhexidine/cetrimide (Savlon®): effects on equilibrium and hearing". The Veterinary Quarterly, vol. 8, No. 1, Jan. 1986, pp. 56-60.
Jacobson, L.S. "Diagnosis and medical treatment of otitis externa in the dog and cat". Journal of the South African Veterinary Medical Association, vol. 73, No. 4, Dec. 2002, pp. 162-170.
Little, Chris; "Medical treatment of otitis externa in the dog and cat". In Practice, vol. 18, No. 2, Jan. 1996, pp. 66-71.
International Search Report and Written Opinion for PCT/EP2011/073566 mailed Mar. 22, 2012.
Spreull, J.S.A., "Treatment of Otitis Media in the Dog". Journal of Small Animla Practice, vol. 5, No. 2, Apr. 1964, pp. 137-152.

* cited by examiner

*Primary Examiner* — Eric Olson
(74) *Attorney, Agent, or Firm* — Michael P. Morris; Joyce L. Morrison

(57) ABSTRACT

The invention relates to a kit-in-part comprising of a composition for the use as a cleaning and treating of ears of a companion animal and suitable packaging material, wherein the kit-in part additionally consists of components selected from the group of a pharmaceutical composition for use in the treatment of otitis externa, application and dosage information, cannules, cotton swabs, gauzes and information about the cleaning and maintenance ears of a companion animal.

19 Claims, No Drawings

KIT-IN-PARTS FOR CLEANING AND TREATING EARS OF COMPANION ANIMALS

FIELD OF THE INVENTION

The present invention is directed to a new kit-in-part containing all components for the treatment and cleaning of ears of an animal, preferably a companion animal, particularly dogs and cats.

BACKGROUND OF THE INVENTION

The field of the invention is that of a kit-in-part containing different otic compositions for the cleaning of inflamed ears prior to the treatment of inflammation such as external otitis and to the treatment of such a condition in an animal, preferably companion animals such as dogs and cats.

Dogs show signs of ear problems when starting to shake his head suddenly. The reason can be amongst others a foreign body, such as for example a grass seed, in the pet's ear. Other foreign organisms such as tiny ear mites can also produce irritation and wax.

Sometimes ear disease is straightforward and easily treated, when caused by a foreign body for example, but many ear problems are recurrent. The ear canal may be very narrow or is lined with plenty of hairs inside so that wax gets trapped. Skin that lines the ears can also give rise to problems such as allergies. The result is excess wax production, inflammation, infection and pain.

Thus regular ear cleaning is vital, especially also as the vigorous head shaking can result in breaking blood vessels in the earflap, which bleeds and forms a blood blister (haematoma). If left, this can form a "cauliflower ear" which interferes with ventilation of the ear canal.

Typical signs in cats that suffer of an ear disease include an unusual odour, scratching or rubbing of ears and head, discharge in the ears, redness or swelling of the ear canal, shaking of the head or tilting it to one side, pain around the ears, and changes in behaviour such as depression or irritability. Ear disease is a common condition in cats.

Inflammation of the outer ear canal is otitis externa. Primary causes of otitis externa include parasites such as ear mites (very common in cats) or foreign bodies. Probably the most common primary cause of otitis externa is allergies, which can be either to inhaled substances (atopy) or food.

Perpetuating factors such as bacterial and fungal infections of the outer ear can increase the severity of the condition and play a major role in chronic or recurrent otitis externa. Otitis media, which is inflammation/infection of the middle ear, is often a source of constant re-infection of the outer ear. One of the most significant perpetuating factors is ear canal hypertrophy (thickening), which may become so severe as to completely close off the outer ear canal and make medical treatment of the ear near impossible.

Treatment of otitis externa has to be according to the underlying, predisposing and perpetuating factors that are present. Treatment options include ear cleaning or flushing, ear medications for infections and steroids to reduce inflammation.

Animals with atopy (inhalant allergy) and food allergies can never be cured and may require continual ear care to minimize a flare up of otitis externa.

Known products for disinfecting purposes make use of chlorhexidine in general as active principle, but its effectiveness depends strongly on concentration.

When chlorhexidine is used at high concentrations, it can result in undesired collateral effects. Other known active principles are iodine compounds that have a wide spectrum of anti-infectives against bacteria, fungi, spores, protozoa, viruses, and yeasts. Aqueous iodine is less effective than alcoholic solutions, but alcoholic component is drying and irritating to abraded skin. Povidone iodine is convenient to use as it is less irritating, but not as effective.

Proper ear cleaning is an important factor as ear medication applied on top of earwax or pus is ineffective and may actually be inactivated. The ear cleaning agent should be mildly antiseptic, dissolve earwax and coat the ear canal to provide long lasting action.

The aim of the invention is to provide a new kit-in-part for companion animals that are in need of ear care for maintenance purposes and/or for the treatment of otitis externa. The kit-in-part is particularly designed for dogs and cats with either non-inflamed or inflamed ears. It is desired to combine components that are absolutely necessary for the purpose of treating the animal's ears more effectively. Furthermore, the kit-in-parts enables pet owners and the veterinarians a convenient method of administration as all needed components for the application is contained within the kit.

DESCRIPTION OF THE INVENTION

The present invention relates to a kit-in part comprising composition A suitable to clean inflamed or non-inflamed ears of an animal and composition B suitable to treat inflamed ears of an animal. The animal to be treated is preferably a companion animal, even more preferred a cat or a dog.

The kit-in-part comprises a composition A, which in turn comprises an antibacterial agent suitable to clean inflamed or non-inflamed ears. The antibacterial agent is selected from the group consisting of cetrimide, chloroxylenol (4-chloro-3,5-dimethylphenol), chlorthymol (4-chloro-5-methyl-2-propan-2-ylphenol), salicylic acid (2-hydroxybenzoic acid), tannin, tetracaine (2-(dimethylamino)ethyl 4-(butylamino)benzoate), chlorhexidine/chlorhexidine gluconate (N',N''''-hexane-1,6-diylbis[N-(4-chlorophenyl)(imidodicarbonimidic diamide)), lactic acid (2-hydroxypropanoic acid) isopropyl alcohol (2-propanol), and combinations thereof, preferably cetrimide.

According to a further aspect, composition A of the kit-in-part comprises medicinal plant derived extracts selected from the group consisiting of *calendula*, *Plantago lanceolata*, witch-hazel/hamamelis, *Matricaria chamomilla*, aloe vera and *Juniperus communis*.

According to a further aspect, composition A of the kit-in-part additionally comprises preferably one or more excipients selected from the group consisting or humectants, wetting agents, humectants and wetting agents.

The humectant that is contained within composition A of the kit-in-part include but not limited to the group consisting of glycerol, polyethylene glycol 200 or 400, peanut oil, almond oil, olive oil and sesame oil, preferably glycerol, polyethylene glycol 200 or 400, even more preferred glycerol.

The wetting agent that is contained within composition A of the kit-in-part is selected from the group consisting of propylene glycol, 1,3-butandiol, ethanol, docusate sodium and dimethyl sulfoxide (DMSO), preferably propylene glycol, docusate sodium and dimethyl sulfoxide (DMSO), even more preferred propylene glycol.

In another aspect, the invention relates to a kit-in-part comprising composition A, which comprises preferably an aqueous solution of propylene glycol, glycerol and cetrimide and composition B. Furthermore, composition A of the kit-in-part has antibacterial properties that are achieved through all three components, whereof one has additional moisturising properties.

Another aspect of the kit-in-part is that composition A as described herein has a pH in the range of pH 4-9, preferably from pH 5-8, most preferred is pH 7. The pH of 7.0 makes sure that all of the components of composition A will be used under optimal conditions to be effective on the environment of the skin. This is one of the advantages of composition A as it therefore does not irritate the skin of the animal. Another advantage of composition A is that it has no odour or smell in any way and therefore does not irritate the sensitive noses of companion animals, especially of dogs and cats.

The following are examples for possible compositions A of the kit-in-parts according to the invention with the following ingredients: (example 1A) chloroxylenol and one or more humectants and/or wetting agent; (example 2A) chlorthymol and one or more humectants and/or wetting agent; (example 3A) salicylic acid and one or more humectants and/or wetting agent; (example 4A) tannin and one or more humectants and/or wetting agent; (example 5A) tetracaine and one or more humectants and/or wetting agent; (example 6A) chlorhexidine/chlorhexidine gluconate and one or more humectants and/or wetting agent; (example 7A) lactic acid and one or more humectants and/or wetting agent; (example 8A) isopropyl alcohol and one or more humectants and/or wetting agent; (example 9A) cetrimide and one or more humectants and/or wetting agent, preferably cetrimide and one or more humectants and/or wetting agent. Preferably the one or more humectants of any of the compositions 1A, 2A, 3A, 4A, 5A, 6A, 7A, 8A or 9A are selected from the group consisting of glycerol, polyethylene glycol 200 or 400, peanut oil, almond oil, olive oil and sesame oil, preferably glycerol (example 10A). Preferably one or more wetting agents of any of the compositions 1A, 2A, 3A, 4A, 5A, 6A, 7A, 8A, 9A or 10A are selected from the group consisting of glycol, 1,3-butandiol, ethanol, docusate sodium and dimethyl sulfoxide (DMSO), preferably propylene glycol (example 11A).

Other examples for composition A of the kit-in-part according to the invention comprise the following ingredients: (example 1Aa) chloroxylenol, *Plantago lanceolata* and one or more humectants and/or wetting agent; (example 2Aa) chloroxylenol, witch-hazel/hamamelis and one or more humectants and/or wetting agent; (example 3Aa) chloroxylenol, *Matricaria chamomilla* and one or more humectants and/or wetting agent; (example 4Aa) chloroxylenol, aloe vera and one or more humectants and/or wetting agent; (example 5Aa) chloroxylenol, *Juniperus communis* and one or more humectants and/or wetting agent; (example 6Aa) chloroxylenol, *calendula* and one or more humectants and/or wetting agent; (example 7Aa) chlorthymol, *Plantago lanceolata* and one or more humectants and/or wetting agent; (example 8Aa) chlorthymol, witch-hazel/hamamelis and one or more humectants and/or wetting agent; (example 9Aa) chlorthymol, *Matricaria chamomilla* and one or more humectants and/or wetting agent; (example 10Aa) chlorthymol, aloe vera and one or more humectants and/or wetting agent; (example 11Aa) chlorthymol, *Juniperus communis* and one or more humectants and/or wetting agent; or (example 12Aa) chlorthymol, *calendula* and one or more humectants and/or wetting agent; (example 13Aa) salicylic acid, *Plantago lanceolata* and one or more humectants and/or wetting agent; (example 14Aa) salicylic acid, witch-hazel/hamamelis and one or more humectants and/or wetting agent; (example 15Aa) salicylic acid, *Matricaria chamomilla* and one or more humectants and/or wetting agent; (example 16Aa) salicylic acid, aloe vera and one or more humectants and/or wetting agent; (example 17Aa) salicylic acid, *Juniperus communis* and one or more humectants and/or wetting agent; or (example 18Aa) salicylic acid, *calendula* and one or more humectants and/or wetting agent; (example 19Aa) tannin, *Plantago lanceolata* and one or more humectants and/or wetting agent; (example 20Aa) tannin, witch-hazel/hamamelis and one or more humectants and/or wetting agent; (example 21Aa) tannin, *Matricaria chamomilla* and one or more humectants and/or wetting agent; (example 22Aa) tannin, aloe vera and one or more humectants and/or wetting agent; (example 23Aa) tannin, *Juniperus communis* and one or more humectants and/or wetting agent; or (example 24Aa) tannin, *calendula* and one or more humectants and/or wetting agent; (example 25Aa) tetracaine, *Plantago lanceolata* and one or more humectants and/or wetting agent; (example 26Aa) tetracaine, witch-hazel/hamamelis and one or more humectants and/or wetting agent; (example 27Aa) tetracaine, *Matricaria chamomilla* and one or more humectants and/or wetting agent; (example 28Aa) tetracaine, aloe vera and one or more humectants and/or wetting agent; (example 29Aa) tetracaine, *Juniperus communis* and one or more humectants and/or wetting agent; or (example 30Aa) tetracaine, *calendula* and one or more humectants and/or wetting agent; (example 31Aa) chlorhexidine/chlorhexidine gluconate, *Plantago lanceolata* and one or more humectants and/or wetting agent; (example 32Aa) chlorhexidine/chlorhexidine gluconate, witch-hazel/hamamelis and one or more humectants and/or wetting agent; (example 33Aa) chlorhexidine/chlorhexidine gluconate, *Matricaria chamomilla* and one or more humectants and/or wetting agent; (example 34Aa) chlorhexidine/chlorhexidine gluconate, aloe vera and one or more humectants and/or wetting agent; (example 35Aa) chlorhexidine/chlorhexidine gluconate, *Juniperus communis* and one or more humectants and/or wetting agent; or (example 36Aa) chlorhexidine/chlorhexidine gluconate, *calendula* and one or more humectants and/or wetting agent; (example 37Aa) lactic acid, *Plantago lanceolata* and one or more humectants and/or wetting agent; (example 38Aa) lactic acid, witch-hazel/hamamelis and one or more humectants and/or wetting agent; (example 39Aa) lactic acid, *Matricaria chamomilla* and one or more humectants and/or wetting agent; (example 40Aa) lactic acid, aloe vera and one or more humectants and/or wetting agent; (example 41Aa) lactic acid, *Juniperus communis* and one or more humectants and/or wetting agent; or (example 42Aa) lactic acid, *calendula* and one or more humectants and/or wetting agent; (example 43Aa) isopropyl alcohol, *Plantago lanceolata* and one or more humectants and/or wetting agent; (example 44Aa) isopropyl alcohol, witch-hazel/hamamelis and one or more humectants and/or wetting agent; (example 45Aa) isopropyl alcohol, *Matricaria chamomilla* and one or more humectants and/or wetting agent; (example 46Aa) isopropyl alcohol, aloe vera and one or more humectants and/or wetting agent, (example 47Aa) isopropyl alcohol, *Juniperus communis* and one or more humectants and/or wetting agent; or (example 48Aa) isopropyl alcohol, *calendula* and one or more humectants and/or wetting agent; (example 49Aa) cetrimide, *Plantago lanceolata* and one or more humectants and/or wetting agent; (example 50Aa) cetrimide, witch-hazel/hamamelis and one or more humectants and/or wetting agent; (example 51Aa) cetrimide, *Matricaria chamomilla* and one or more humectants and/or wetting agent; (example 52Aa) cetrimide, aloe vera and one or more humectants and/or wetting agent; (example 53Aa) cetrimide, *Juniperus communis* and one or more humectants and/or wetting agent; or (example 54Aa) cetrimide, *calendula* and one or more humectants and/or wetting agent. Preferably one or more of the humectants of compositions 1Aa, 2Aa, 3Aa, 4Aa, 5Aa, 6Aa, 7Aa, 8Aa, 9Aa, 10Aa, 11Aa, 12 Aa, . . . , 45Aa, 46Aa, 47Aa, 48Aa, 49Aa, 50Aa, 51Aa, 52Aa, 53Aa, 54Aa, are selected from the group consisting of glycerol, polyethylene glycol 200 or 400, peanut oil, almond oil, olive oil and sesame oil, preferably glycerol (example 55Aa). Preferably one or more wetting agents of any of the compositions 1Aa, 2Aa, 3Aa, 4Aa, 5Aa, 6Aa, 7Aa, 8Aa, 9Aa, 10Aa, 11Aa, 12Aa, . . . , 45Aa, 46Aa, 47Aa, 48Aa, 49Aa, 50Aa, 51Aa, 52Aa, 53Aa, 54Aa, 55Aa, are selected from the group consisting of glycol, 1,3-butandiol, ethanol, docusate sodium and dimethyl sulfoxide (DMSO), preferably propylene glycol (example 56Aa).

Composition A of the kit-in-part is herein defined to include all above defined examples for composition A and composition Aa. Thus composition A of the kit-in-part is referring to examples 1A, 2A, 3A, 4A, 5A, 6A, 7A, 8A, 9A, 10A, 11A, 1 Aa, 2Aa, 3Aa, 4Aa, 5Aa, 6Aa, 7Aa, 8Aa, 9Aa, 10Aa, 11Aa, 12 Aa, . . . , 45Aa, 46Aa, 47Aa, 48Aa, 49Aa, 50Aa, 51Aa, 52Aa, 53Aa, 54Aa, 55Aa, 56Aa.

According to a further aspect, composition A of the kit-in-part as defined above is contained within a bottle with a volume of 25 to 500 ml, 50 to 400 ml, 50 to 300 ml, 50 to 200 ml or 100 ml, preferably 100 ml. Administration of the above described composition A of the kit-in-part can occur 1 to 7 times a day, preferably 2 to 6, even more preferred 3 to 5 times per day. The amount to be used of the composition in each cleaning procedure/application is 1 to 50 ml.

The kit-in-part defined above also contains composition B that comprises one or more active pharmaceutical ingredients such as antimicrobial agents and/or corticoids for the treatment of inflamed ears.

Said antimicrobial agent is selected from the group consisting of antiparasitics, antibiotics and antifungal agents.

Thus, compostion B of the kit-in-part comprises one or more antibiotics, one or more antifungal, one or more antiparasitics, one or more corticoids, or combinations thereof such as for example a corticoids and an antifungal and an antibiotic and an antiparasitic, or corticoid and antibiotic and antiparasitic, corticoid and antifungal and antiparasitic, or corticoid and antifungal, corticoid and antiparasitic, corticoid and antibiotics, or antifungal and antiparasitic, antifungal and antibiotic, antibiotic and antiparasitic. Preferably composition B of the kit-in-part contains one or more antibiotics, a corticoid and an antifungal. According to a further aspect, composition B of the kit-in-part comprises one or more excipient.

The corticosteroid that is contained in composition B is selected from the group consisting of prednisone or its metabolite prednisolone or a pharmaceutically acceptable salt of any of these two compounds, dexamethasone, triamcinolone, hydrocortisone aceponate and betamethasone, preferably prednisone or its metabolite prednisolone or a pharmaceutically acceptable salt of any of these two compounds.

The antibiotic that is contained in composition B is selected from the group consisting of polymyxin, marbofloxacin, neomycin, thiostrepton, gentamicin, chloramphenicole, sodium fusidate and framycetin sulphate, preferably sodium fusidate and framycetin sulphate.

The antifungal agent that is contained in composition B is selected from the group consisting of miconazole, clotrimazole and nystatin.

The excipients that are contained in composition B is a dispersion medium or solvent as for example but not limiting to highly disperse silicon dioxide, paraffin, mineral oils, polyethylene, triglycerides or propylene glycol.

According to another aspect, kit-in-part comprises composition A as defined above and composition B, wherein composition B comprises a corticoid and/or an antibiotic and/or an antifungal agent as well as one or more humectants and/or wetting agent. Preferably, the corticoid and/or an antibiotic and/or an antifungal agent are selected from those described herein. Even more preferred, composition B of the-kit-in part comprise sodium fusidate, framycetin sulphate, prednisolone and nystatin.

The following are examples for composition B of the kit-in-part according to the invention: (example 1B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably polymyxin and marbofloxacin, polymyxin and neomycin, polymyxin and thiostrepton, polymyxin and gentamicin, polymyxin and chloramphenicole, polymyxin and sodium fusidate or polymyxin and framycetin sulphate, and one or more excipient; (example 2B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably marbofloxacin and neomycin, marbofloxacin and thiostrepton, marbofloxacin and gentamicin, marbofloxacin and chloramphenicole, marbofloxacin and sodium fusidate or marbofloxacin and framycetin sulphate, and one or more excipient; (example 3B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably neomycin and thiostrepton, neomycin and gentamicin, neomycin and chloramphenicole, neomycin and sodium fusidate or neomycin and framycetin sulphate, and one or more excipient; (example 4B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 5B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 6B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably gentamicin and chloramphenicole, gentamicin and sodium fusidate or gentamicin and framycetin sulphate, and one or more excipient; (example 7B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably chloramphenicole and sodium fusidate or chloramphenicole and framycetin sulphate, and one or more excipient; (example 8B) prednisone, its metabolite prednisolone or a pharmaceutically acceptable salt of any of these two compounds and one or more antibiotic selected from the group consisting of polymyxin, marbofloxacin, neomycin, thiostrepton, gentamicin, chloramphenicole, sodium fusidate and framycetin sulphate, preferably sodium fusidate and framycetin sulphate, and one or more excipient; (example 9B) dexamethasone and one or more antibiotic selected from the group consisting of polymyxin, marbofloxacin, neomycin, thiostrepton, gentamicin, chloramphenicole, sodium fusidate and framycetin sulphate, preferably polymyxin and marbofloxacin, polymyxin and neomycin, polymyxin and thiostrepton, polymyxin and gentamicin, polymyxin and chloramphenicole, polymyxin and sodium fusidate or polymyxin and framycetin sulphate, and one or more excipient; (example 10B) dexamethasone and one or more antibiotic selected from the group consisting of polymyxin, marbofloxacin, neomycin, thiostrepton, gentamicin, chloramphenicole, sodium fusidate and framycetin sulphate, preferably marbofloxacin and neomycin, marbofloxacin and thiostrepton, marbofloxacin and gentamicin, marbofloxacin and chloramphenicole, marbofloxacin and sodium fusidate or marbofloxacin and framycetin sulphate, and one or more excipient; (example 11B) dexamethasone and one or more antibiotic selected from the group consisting of polymyxin, marbofloxacin, neomycin, thiostrepton, gentamicin, chloramphenicole, sodium fusidate and framycetin sulphate, preferably neomycin and thiostrepton, neomycin and gentamicin, neomycin and chloramphenicole, neomycin and sodium fusidate or neomycin and framycetin sulphate, and one or more excipient; (example 12B) dexamethasone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 13B) dexamethasone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 14B) dexamethasone and one or more antibiotic selected from the group consisting of polymyxin, marbofloxacin, neomycin, thiostrepton, gentamicin, chloramphenicole, sodium fusidate and framycetin sulphate, preferably gentamicin and chloramphenicole, gentamicin and sodium fusidate or gentamicin and framycetin sulphate, and one or more excipient; (example 15B) dexamethasone and one or more antibiotic selected from the group consisting of polymyxin, marbofloxacin, neomycin, thiostrepton, gentamicin, chloramphenicole, sodium fusidate and framycetin sulphate, preferably chloramphenicole and sodium fusidate or chloramphenicole and framycetin sulphate, and one or more excipient; (example 16B) dexamethasone and one or more antibiotic selected from the group consisting of polymyxin, marbofloxacin, neomycin, thiostrepton, gentamicin, chloramphenicole, sodium fusidate and framycetin sulphate, preferably sodium fusidate and framycetin sulphate, and one or more excipient; (example 17B) triamcinolone and one or more antibiotic selected from the group consisting of polymyxin, marbofloxacin, neomycin, thiostrepton, gentamicin, chloramphenicole, sodium fusidate and framycetin sulphate, preferably polymyxin and marbofloxacin, polymyxin and neomycin, polymyxin and thiostrepton, polymyxin and gentamicin, polymyxin and chloramphenicole, polymyxin and sodium fusidate or polymyxin and framycetin sulphate, and one or more excipient; (example 18B) triamcinolone and one or more antibiotic selected from the group consisting of polymyxin, marbofloxacin, neomycin, thiostrepton, gentamicin, chloramphenicole, sodium fusidate and framycetin sulphate, preferably marbofloxacin and neomycin, marbofloxacin and thiostrepton, marbofloxacin and gentamicin, marbofloxacin and chloramphenicole, marbofloxacin and sodium fusidate or marbofloxacin and framycetin sulphate, and one or more excipient; (example 19B) triamcinolone and one or more antibiotic selected from the group consisting of polymyxin, marbofloxacin, neomycin, thiostrepton, gentamicin, chloramphenicole, sodium fusidate and framycetin sulphate, preferably neomycin and thiostrepton, neomycin and gentamicin, neomycin and chloramphenicole, neomycin and sodium fusidate or neomycin and framycetin sulphate, and one or more excipient; (example 20B) triamcinolone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 21B) triamcinolone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 22B) triamcinolone and one or more antibiotic selected from the group consisting of polymyxin, marbofloxacin, neomycin, thiostrepton, gentamicin, chloramphenicole, sodium fusidate and framycetin sulphate, preferably gentamicin and chloramphenicole, gentamicin and sodium fusidate or gentamicin and framycetin sulphate, and one or more excipient; (example 23B) triamcinolone and one or more antibiotic selected from the group consisting of polymyxin, marbofloxacin, neomycin, thiostrepton, gentamicin, chloramphenicole, sodium fusidate and framycetin sulphate, preferably chloramphenicole and sodium fusidate or chloramphenicole and framycetin sulphate, and one or more excipient; (example 24B) triamcinolone and one or more antibiotic selected from the group consisting of polymyxin, marbofloxacin, neomycin, thiostrepton, gentamicin, chloramphenicole, sodium fusidate and framycetin sulphate, preferably sodium fusidate and framycetin sulphate, and one or more excipient; (example 25B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably polymyxin and marbofloxacin, polymyxin and neomycin, polymyxin and thiostrepton, polymyxin and gentamicin, polymyxin and chloramphenicole, polymyxin and sodium fusidate or polymyxin and framycetin sulphate, and one or more excipient; (example 26B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably marbofloxacin and neomycin, marbofloxacin and thiostrepton, marbofloxacin and gentamicin, marbofloxacin and chloramphenicole, marbofloxacin and sodium fusidate or marbofloxacin and framycetin sulphate, and one or more excipient; (example 27B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably neomycin and thiostrepton, neomycin and gentamicin, neomycin and chloramphenicole, neomycin and sodium fusidate or neomycin and framycetin sulphate, and one or more excipient; (example 28B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 29B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 30B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably gentamicin and chloramphenicole, gentamicin and sodium fusidate or gentamicin and framycetin sulphate, and one or more excipient; (example 31B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably chloramphenicole and sodium fusidate or chloramphenicole and framycetin sulphate, and one or more excipient; (example 32B) hydrocortisone derivatives such as hydrocortisone aceponate and one or more antibiotic selected from the group consisting of polymyxin, marbofloxacin, neomycin, thiostrepton, gentamicin, chloramphenicole, sodium fusidate and framycetin sulphate, preferably sodium fusidate and framycetin sulphate, and one or more excipient; (example 33B) betamethasone and one or more antibiotic selected from the group consisting of polymyxin, marbofloxacin, neomycin, thiostrepton, gentamicin, chloramphenicole, sodium fusidate and framycetin sulphate, preferably polymyxin and marbofloxacin, polymyxin and neomycin, polymyxin and thiostrepton, polymyxin and gentamicin, polymyxin and chloramphenicole, polymyxin and sodium fusidate or polymyxin and framycetin sulphate, and one or more excipient; (example 34B) betamethasone and one or more antibiotic selected from the group consisting of polymyxin, marbofloxacin, neomycin, thiostrepton, gentamicin, chloramphenicole, sodium fusidate and framycetin sulphate, preferably marbofloxacin and neomycin, marbofloxacin and thiostrepton, marbofloxacin and gentamicin, marbofloxacin and chloramphenicole, marbofloxacin and sodium fusidate or marbofloxacin and framycetin sulphate, and one or more excipient; (example 35B) betamethasone and one or more antibiotic selected from the group consisting of polymyxin, marbofloxacin, neomycin, thiostrepton, gentamicin, chloramphenicole, sodium fusidate and framycetin sulphate, preferably neomycin and thiostrepton, neomycin and gentamicin, neomycin and chloramphenicole, neomycin and sodium fusidate or neomycin and framycetin sulphate, and one or more excipient; (example 36B) betamethasone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 37B) betamethasone and one or more antibiotic selected from the group consisting of polymyxin, marbofloxacin, neomycin, thiostrepton, gentamicin, chloramphenicole, sodium fusidate and framycetin sulphate, preferably thiostrepton and gentamicin, thiostrepton and chloramphenicole, thiostrepton and sodium fusidate or thiostrepton and framycetin sulphate, and one or more excipient; (example 38B) betamethasone and one or more antibiotic selected from the group consisting of polymyxin, marbofloxacin, neomycin, thiostrepton, gentamicin, chloramphenicole, sodium fusidate and framycetin sulphate, preferably gentamicin and chloramphenicole, gentamicin and sodium fusidate or gentamicin and framycetin sulphate, and one or more excipient; (example 39B) betamethasone and one or more antibiotic selected from the group consisting of polymyxin, marbofloxacin, neomycin, thiostrepton, gentamicin, chloramphenicole, sodium fusidate and framycetin sulphate, preferably chloramphenicole and sodium fusidate or chloramphenicole and framycetin sulphate, and one or more excipient; (example 40B) betamethasone and one or more antibiotic selected from the group consisting of polymyxin, marbofloxacin, neomycin, thiostrepton, gentamicin, chloramphenicole, sodium fusidate and framycetin sulphate, preferably sodium fusidate and framycetin sulphate, and one or more excipient. Preferably one or more excipients of composition 1B, 2B, 3B, 4B, 5B, 6B, 7B, 8B, 9B, . . . , 32B, 33B, 34B, 35B, 36B, 37B, 38B, 39B, 40B are dispersion medium or solvent as for example but not limiting to highly disperse silicon dioxide, paraffin, mineral oils, polyethylene, triglycerides or propylene glycol (example 41B).

According to a further aspect, composition B including any of the above defined examples 1B, 2B, 3B, 4B, 5B, 6B, 7B, 8B, 9B, . . . , 32B, 33B, 34B, 35B, 36B, 37B, 38B, 39B, 40B, 41B, comprises antifungal agents as for example given in (example 1C) comprising 1B and an antifungal agent selected from the group consisting of miconazole, clotrimazole and nystatin; (example 2C) comprising 2B and an antifungal agent selected from the group consisting of miconazole, clotrimazole and nystatin; (example 3C) comprising 3B and an antifungal agent selected from the group consisting of miconazole, clotrimazole and nystatin; (example 4C) comprising 4B and an antifungal agent selected from the group consisting of miconazole, clotrimazole and nystatin; (example 5C) comprising 5B and an antifungal agent selected from the group consisting of miconazole, clotrimazole and nystatin; (example 6C) comprising 6B and an antifungal agent selected from the group consisting of miconazole, clotrimazole and nystatin; (example 7C) comprising 7B and an antifungal agent selected from the group consisting of miconazole, clotrimazole and nystatin; (example 8C) comprising 8B and an antifungal agent selected from the group consisting of miconazole, clotrimazole and nystatin; (example 9C) comprising 9B and an antifungal agent selected from the group consisting of miconazole, clotrimazole and nystatin; (example 10C) comprising 10B and an antifungal agent selected from the group consisting of miconazole, clotrimazole and nystatin; (example 11C) comprising 11B and an antifungal agent selected from the group consisting of miconazole, clotrimazole and nystatin; (example 12C) comprising 12B and an antifungal agent selected from the group consisting of miconazole, clotrimazole and nystatin; (example 13C) comprising 13B and an antifungal agent selected from the group consisting of miconazole, clotrimazole and nystatin; (example 14C) comprising 14B and an antifungal agent selected from the group consisting of miconazole, clotrimazole and nystatin; (example 15C) comprising 15B and an antifungal agent selected from the group consisting of miconazole, clotrimazole and nystatin; (example 16C) comprising 16B and an antifungal agent selected from the group consisting of miconazole, clotrimazole and nystatin; (example 17C) comprising 17B and an antifungal agent selected from the group consisting of miconazole, clotrimazole and nystatin; (example 18C) comprising 18B and an antifungal agent selected from the group consisting of miconazole, clotrimazole and nystatin; (example 19C) comprising 19B and an antifungal agent selected from the group consisting of miconazole, clotrimazole and nystatin; (example 20C) comprising 20B and an antifungal agent selected from the group consisting of miconazole, clotrimazole and nystatin; (example 21C) comprising 21B and an antifungal agent selected from the group consisting of miconazole, clotrimazole and nystatin; (example 22C) comprising 22B and an antifungal agent selected from the group consisting of miconazole, clotrimazole and nystatin; (example 23C) comprising 23B and an antifungal agent selected from the group consisting of miconazole, clotrimazole and nystatin; (example 24C) comprising 24B and an antifungal agent selected from the group consisting of miconazole, clotrimazole and nystatin; (example 25C) comprising 25B and an antifungal agent selected from the group consisting of miconazole, clotrimazole and nystatin; (example 26C) comprising 26B and an antifungal agent selected from the group consisting of miconazole, clotrimazole and nystatin; (example 27C) comprising 27B and an antifungal agent selected from the group consisting of miconazole, clotrimazole and nystatin; (example 28C) comprising 28B and an antifungal agent selected from the group consisting of miconazole, clotrimazole and nystatin; (example 29C) comprising 29B and an antifungal agent selected from the group consisting of miconazole, clotrimazole and nystatin; (example 30C) comprising 30B and an antifungal agent selected from the group consisting of miconazole, clotrimazole and nystatin; (example 31C) comprising 31B and an antifungal agent selected from the group consisting of miconazole, clotrimazole and nystatin; (example 32C) comprising 32B and an antifungal agent selected from the group consisting of miconazole, clotrimazole and nystatin; (example 33C) comprising 33B and an antifungal agent selected from the group consisting of miconazole, clotrimazole and nystatin; (example 34C) comprising 34B and an antifungal agent selected from the group consisting of miconazole, clotrimazole and nystatin; (example 35C) comprising 35B and an antifungal agent selected from the group consisting of miconazole, clotrimazole and nystatin; (example 36C) comprising 36B and an antifungal agent selected from the group consisting of miconazole, clotrimazole and nystatin; (example 37C) comprising 37B and an antifungal agent selected from the group consisting of miconazole, clotrimazole and nystatin; (example 38C) comprising 38B and an antifungal agent selected from the group consisting of miconazole, clotrimazole and nystatin; (example 39C) comprising 39B and an antifungal agent selected from the group consisting of miconazole, clotrimazole and nystatin; (example 40C) comprising 40B and an antifungal agent selected from the group consisting of miconazole, clotrimazole and nystatin, (example 41C) comprising 41B and an antifungal agent selected from the group consisting of miconazole, clotrimazole and nystatin.

Composition B of the kit-in-part is herein defined to include all above defined examples for composition B and composition C. Thus composition B of the kit-in-part is referring to examples 1B, 2B, 3B, 4B, 5B, 6B, 7B, 8B, 9B, . . . , 32B, 33B, 34B, 35B, 36B, 37B, 38B, 39B, 40B, 41B or 1C, 2C, 3C, 4C, 5C, 6C, 7C, 8C, 9C, . . . , 32C, 33C, 34C, 35C, 36C, 37C, 38C, 39C, 40C, 41C.

In another aspect of the invention composition B, including 1B, 2B, 3B, 4B, 5B, 6B, 7B, 8B, 9B, . . . , 32B, 33B, 34B, 35B, 36B, 37B, 38B, 39B, 40B, 41B or 1C, 2C, 3C, 4C, 5C, 6C, 7C, 8C, 9C, . . . , 32C, 33C, 34C, 35C, 36C, 37C, 38C, 39C, 40C, of the kit-in-part is a suspension preferably comprising sodium fusidate, framycetin sulphate, prenisolone and nystatin.

Composition A and B that are contained within the kit-in-part according to the invention have constituents as described above. Thus combinations of all above described examples are possible resulting in the following list I: example 1A combined with example 1B or example 1C, example 1A combined with example 2B or example 2C; 1A combined with example 3B or example 3C; 1A combined with example 4B or example 4C; 1A combined with example 5B or example 5C; 1A combined with example 6B or example 6C; 1A combined with example 7B or example 7C; 1A combined with example 8B or example 8C; 1A combined with example 9B or example 9C; 1A combined with example 10B or example 10C; 1A combined with example 11B or example 11C; 1A combined with example 12B or example 12C; 1A combined with example 13B or example 13C; 1A combined with example 14B or example 14C; 1A combined with example 15B or example 15C; 1A combined with example 16B or example 16C; 1A combined with example 17B or example 17C; 1A combined with example 18B or example 18C; 1A combined with example 19B or example 19C; 1A combined with example 20B or example 20C; 1A combined with example 21B or example 21C; 1A combined with example 22B or example 22C; 1A combined with example 23B or example 23C; 1A combined with example 24B or example 24C; 1A combined with example 25B or example 25C; 1A combined with example 26B or example 26C; 1A combined with example 27B or example 27C; 1A combined with example 28B or example 28C; 1A combined with example 29B or example 29C; 1A combined with example 30B or example 30C; 1A combined with example 31B or example 31C; 1A combined with example 32B or example 32C; 1A combined with example 33B or example 33C; 1A combined with example 34B or example 34C; 1A combined with example 35B or example 35C; 1A combined with example 36B or example 36C; 1A combined with example 37B or example 37C; 1A combined with example 38B or example 38C; 1A combined with example 39B or example 39C; 1A combined with example 40B or example 40C; 1A combined with example 41B or example 41C.

Example 2A combined with example 1B or example 1C; example 2A combined with example 2B or example 2C; 2A combined with example 3B or example 3C; 2A combined with example 4B or example 4C; 2A combined with example 5B or example 5C; 2A combined with example 6B or example 6C; 2A combined with example 7B or example 7C; 2A combined with example 8B or example 8C; 2A combined with example 9B or example 9C; 2A combined with example 10B or example 10C; 2A combined with example 11B or example 11C; 2A combined with example 12B or example 12C; 2A combined with example 13B or example 13C; 2A combined with example 14B or example 14C; 2A combined with example 15B or example 15C; 2A combined with example 16B or example 16C; 2A combined with example 17B or example 17C; 2A combined with example 18B or example 18C; 2A combined with example 19B or example 19C; 2A combined with example 20B or example 20C; 2A combined with example 21B or example 21C; 2A combined with example 22B or example 22C; 2A combined with example 23B or example 23C; 2A combined with example 24B or example 24C; 2A combined with example 25B or example 25C; 2A combined with example 26B or example 26C; 2A combined with example 27B or example 27C; 2A combined with example 28B or example 28C; 2A combined with example 29B or example 29C; 2A combined with example 30B or example 30C; 2A combined with example 31B or example 31C; 2A combined with example 32B or example 32C; 2A combined with example 33B or example 33C; 2A combined with example 34B or example 34C; 2A combined with example 35B or example 35C; 2A combined with example 36B or example 36C; 2A combined with example 37B or example 37C; 2A combined with example 38B or example 38C; 2A combined with example 39B or example 39C; 2A combined with example 40B or example 40C; 2A combined with example 41B or example 41C.

Example 3A combined with example 1B or example 1C; example 3A combined with example 2B or example 2C; 3A combined with example 3B or example 3C; 3A combined with example 4B or example 4C; 3A combined with example 5B or example 5C; 3A combined with example 6B or example 6C; 3A combined with example 7B or example 7C; 3A combined with example 8B or example 8C; 3A combined with example 9B or example 9C; 3A combined with example 10B or example 10C; 3A combined with example 11B or example 11C; 3A combined with example 12B or example 12C; 3A combined with example 13B or example 13C; 3A combined with example 14B or example 14C; 3A combined with example 15B or example 15C; 3A combined with example 16B or example 16C; 3A combined with example 17B or example 17C; 3A combined with example 18B or example 18C; 3A combined with example 19B or example 19C; 3A combined with example 20B or example 20C; 3A combined with example 21B or example 21C; 3A combined with example 22B or example 22C; 3A combined with example 23B or example 23C; 3A combined with example 24B or example 24C; 3A combined with example 25B or example 25C; 3A combined with example 26B or example 26C; 3A combined with example 27B or example 27C; 3A combined with example 28B or example 28C; 3A combined with example 29B or example 29C; 3A combined with example 30B or example 30C; 3A combined with example 31B or example 31C; 3A combined with example 32B or example 32C; 3A combined with example 33B or example 33C; 3A combined with example 34B or example 34C; 3A combined with example 35B or example 35C; 3A combined with example 36B or example 36C; 3A combined with example 37B or example 37C; 3A combined with example 38B or example 38C; 3A combined with example 39B or example 39C; 3A combined with example 40B or example 40C; 3A combined with example 41B or example 41C.

Example 4A combined with example 1B or example 1C; example 4A combined with example 2B or example 2C; 4A combined with example 3B or example 3C; 4A combined with example 4B or example 4C; 4A combined with example 5B or example 5C; 1A combined with example 6B or example 6C; 4A combined with example 7B or example 7C; 4A combined with example 8B or example 8C; 4A combined with example 9B or example 9C; 4A combined with example 10B or example 10C; 4A combined with example 11B or example 11C; 4A combined with example 12B or example 12C; 4A combined with example 13B or example 13C; 4A combined with example 14B or example 14C; 4A combined with example 15B or example 15C; 4A combined with example 16B or example 16C; 4A combined with example 17B or example 17C; 4A combined with example 18B or example 18C; 4A combined with example 19B or example 19C; 4A combined with example 20B or example 20C; 4A combined with example 21B or example 21C; 4A combined with example 22B or example 22C; 4A combined with example 23B or example 23C; 4A combined, with example 24B or example 24C; 4A combined with example 25B or example 25C; 4A combined with example 26B or example 26C; 4A combined with example 27B or example 27C; 4A combined with example 28B or example 28C; 4A combined with example 29B or example 29C; 4A combined with example 30B or example 30C; 4A combined with example 31B or example 31C; 4A combined with example 32B or example 32C; 4A combined with example 33B or example 33C; 4A combined with example 34B or example 34C; 4A combined with example 35B or example 35C; 4A combined with example 36B or example 36C; 4A combined with example 37B or example 37C; 4A combined with example 38B or example 38C; 4A combined with example 39B or example 39C; 4A combined with example 40B or example 40C; 4A combined with example 41B or example 41C.

Example 5A combined with example 1B or example 1C; example 5A combined with example 2B or example 2C; 5A combined with example 3B or example 3C; 5A combined with example 4B or example 4C; 5A combined with example 5B or example 5C; 5A combined with example 6B or example 6C; 5A combined with example 7B or example 7C; 5A combined with example 8B or example 8C; 5A combined with example 9B or example 9C; 5A combined with example 10B or example 10C; 5A combined with example 11B or example 11C; 5A combined with example 12B or example 12C; 5A combined with example 13B or example 13C; 5A combined with example 14B or example 14C; 5A combined with example 15B or example 15C; 5A combined with example 16B or example 16C; 5A combined with example 17B or example 17C; 5A combined with example 18B or example 18C; 5A combined with example 19B or example 19C; 5A combined with example 20B or example 20C; 5A combined with example 21B or example 21C; 5A combined with example 22B or example 22C; 5A combined with example 23B or example 23C; 5A combined with example 24B or example 24C; 5A combined with example 25B or example 25C; 5A combined with example 26B or example 26C; 5A combined with example 27B or example 27C; 5A combined with example 28B or example 28C; 5A combined with example 29B or example 29C; 5A combined with example 30B or example 30C; 5A combined with example 31B or example 31C; 5A combined with example 32B or example 32C; 5A combined with example 33B or example 33C; 5A combined with example 34B or example 34C; 5A combined with example 35B or example 35C; 5A combined with example 36B or example 36C; 5A combined with example 37B or example 37C; 5A combined with example 38B or example 38C; 5A combined with example 39B or example 39C; 5A combined with example 40B or example 40C; 5A combined with example 41B or example 41C.

Example 6A combined with example 1B or example 1C; example 6A combined with example 2B or example 2C; 6A combined with example 3B or example 3C; 6A combined with example 4B or example 4C; 6A combined with example 5B or example 5C; 6A combined with example 6B or example 6C; 6A combined with example 7B or example 7C; 6A combined with example 8B or example 8C; 6A combined with example 9B or example 9C; 6A combined with example 10B or example 10C; 6A combined with example 11B or example 11C; 6A combined with example 12B or example 12C; 6A combined with example 13B or example 13C; 6A combined with example 14B or example 14C; 6A combined with example 15B or example 15C; 6A combined with example 16B or example 16C; 6A combined with example 17B or example 17C; 6A combined with example 18B or example 18C; 6A combined with example 19B or example 19C; 6A combined with example 20B or example 20C; 6A combined with example 21B or example 21C; 6A combined with example 22B or example 22C; 6A combined with example 23B or example 23C; 6A combined with example 24B or example 24C; 6A combined with example 25B or example 25C; 6A combined with example 26B or example 26C; 6A combined with example 27B or example 27C; 6A combined with example 28B or example 28C; 6A combined with example 29B or example 29C; 6A combined with example 30B or example 30C; 6A combined with example 31B or example 31C; 6A combined with example 32B or example 32C; 6A combined with example 33B or example 33C; 6A combined with example 34B or example 34C; 6A combined with example 35B or example 35C; 6A combined with example 36B or example 36C; 6A combined with example 37B or example 37C; 6A combined with example 38B or example 38C; 1A combined with example 39B or example 39C; 6A combined with example 40B or example 40C; 6A combined with example 41B or example 41C.

Example 7A combined with example 1B or example 1C; example 7A combined with example 2B or example 2C; 7A combined with example 3B or example 3C; 7A combined with example 4B or example 4C; 7A combined with example 5B or example 5C; 7A combined with example 6B or example 6C; 7A combined with example 7B or example 7C; 7A combined with example 8B or example 8C; 7A combined with example 9B or example 9C; 7A combined with example 10B or example 10C; 7A combined with example 11B or example 11C; 7A combined with example 12B or example 12C; 7A combined with example 13B or example 13C; 7A combined with example 14B or example 14C; 1A combined with example 15B or example 15C; 7A combined with example 16B or example 16C; 1A combined with example 17B or example 17C; 7A combined with example 18B or example 18C; 7A combined with example 19B or example 19C; 7A combined with example 20B or example 20C; 7A combined with example 21B or example 21C; 7A combined with example 22B or example 22C; 7A combined with example 23B or example 23C; 7A combined with example 24B or example 24C; 7A combined with example 25B or example 25C; 7A combined with example 26B or example 26C; 7A combined with example 27B or example 27C; 7A combined with example 28B or example 28C; 7A combined with example 29B or example 29C; 7A combined with example 30B or example 30C; 7A combined with example 31B or example 31C; 7A combined with example 32B or example 32C; 7A combined with example 33B or example 33C; 7A combined with example 34B or example 34C; 7A combined with example 35B or example 35C; 7A combined with example 36B or example 36C; 7A combined with example 37B or example 37C; 7A combined with example 38B or example 38C; 7A combined with example 39B or example 39C; 7A combined with example 40B or example 40C; 7A combined with example 41B or example 41C.

Example 8A combined with example 1B or example 1C; example 8A combined with example 2B or example 2C; 8A combined with example 3B or example 3C; 8A combined with example 4B or example 4C; 8A combined with example 5B or example 5C; 8A combined with example 6B or example 6C; 8A combined with example 7B or example 7C; 8A combined with example 8B or example 8C; 8A combined with example 9B or example 9C; 8A combined with example 10B or example 10C; 8A combined with example 11B or example 11C; 8A combined with example 12B or example 12C; 8A combined with example 13B or example 13C; 8A combined with example 14B or example 14C; 8A combined with example 15B or example 15C; 8A combined with example 16B or example 16C; 8A combined with example 17B or example 17C; 8A combined with example 18B or example 18C; 8A combined with example 19B or example 19C; 8A combined with example 20B or example 20C; 8A combined with example 21B or example 21C; 8A combined with example 22B or example 22C; 8A combined with example 23B or example 23C; 8A combined with example 24B or example 24C; 8A combined with example 25B or example 25C; 8A combined with example 26B or example 26C; 8A combined with example 27B or example 27C; 8A combined with example 28B or example 28C; 8A combined with example 29B or example 29C; 8A combined with example 30B or example 30C; 8A combined with example 31B or example 31C; 8A combined with example 32B or example 32C; 8A combined with example 33B or example 33C; 8A combined with example 34B or example 34C; 8A combined with example 35B or example 35C; 8A combined with example 36B or example 36C; 8A combined with example 37B or example 37C; 8A combined with example 38B or example 38C; 8A combined with example 39B or example 39C; 8A combined with example 40B or example 40C; 8A combined with example 41B or example 41C.

Example 9A combined with example 1B or example 1C; example 9A combined with example 2B or example 2C; 9A combined with example 3B or example 3C; 9A combined with example 4B or example 4C; 9A combined with example 5B or example 5C; 9A combined with example 6B or example 6C; 9A combined with example 7B or example 7C; 9A combined with example 8B or example 8C; 9A combined with example 9B or example 9C; 9A combined with example 10B or example 10C; 9A combined with example 11B or example 11C; 9A combined with example 12B or example 12C; 9A combined with example 13B or example 13C; 9A combined with example 14B or example 14C; 9A combined with example 15B or example 15C; 9A combined with example 16B or example 16C; 9A combined with example 17B or example 17C; 9A combined with example 18B or example 18C; 9A combined with example 19B or example 19C; 9A combined with example 20B or example 20C; 9A combined with example 21B or example 21C; 9A combined with example 22B or example 22C; 9A combined with example 23B or example 23C; 9A combined with example 24B or example 24C; 9A combined with example 25B or example 25C; 9A combined with example 26B or example 26C; 9A combined with example 27B or example 27C; 9A combined with example 28B or example 28C; 9A combined with example 29B or example 29C; 9A combined with example 30B or example 30C; 9A combined with example 31B or example 31C; 9A combined with example 32B or example 32C; 9A combined with example 33B or example 33C; 9A combined with example 34B or example 34C; 9A combined with example 35B or example 35C; 9A combined with example 36B or example 36C; 9A combined with example 37B or example 37C; 9A combined with example 38B or example 38C; 9A combined with example 39B or example 39C; 9A combined with example 40B or example 40C; 9A combined with example 41B or example 41C.

Example 10A combined with example 1B or example 1C; example 10A combined with example 2B or example 2C; 2A combined with example 3B or example 3C; 10A combined with example 4B or example 4C; 10A combined with example 5B or example 5C; 10A combined with example 6B or example 6C; 10A combined with example 7B or example 7C; 10A combined with example 8B or example 8C; 10A combined with example 9B or example 9C; 10A combined with example 10B or example 10C; 10A combined with example 11B or example 11C; 10A combined with example 12B or example 12C; 10A combined with example 13B or example 13C; 10A combined with example 14B or example 14C; 10A combined with example 15B or example 15C; 10A combined with example 16B or example 16C; 10A combined with example 17B or example 17C; 10A combined with example 18B or example 18C; 10A combined with example 19B or example 19C; 10A combined with example 20B or example 20C; 10A combined with example 21B or example 21C; 10A combined with example 22B or example 22C; 2A combined with example 23B or example 23C; 10A combined with example 24B or example 24C; 10A combined with example 25B or example 25C; 10A combined with example 26B or example 26C; 10A combined with example 27B or example 27C; 10A combined with example 28B or example 28C; 10A combined with example 29B or example 29C; 10A combined with example 30B or example 30C; 10A combined with example 318 or example 31C; 10A combined with example 32B or example 32C; 10A combined with example 33B or example 33C; 2A combined with example 34B or example 34C; 10A combined with example 35B or example 35C; 10A combined with example 36B or example 36C; 10A combined with example 37B or example 37C; 10A combined with example 38B or example 38C; 10A combined with example 39B or example 39C; 10A combined with example 40B or example 40C; 10A combined with example 418 or example 41C.

Example 11A combined with example 1B or example 1C; example 11A combined with example 2B or example 2C; 11A combined with example 3B or example 3C; 11A combined with example 4B or example 4C; 11A combined with example 5B or example 5C; 11A combined with example 6B or example 6C; 11A combined with example 7B or example 7C; 11A combined with example 8B or example 8C; 11A combined with example 9B or example 9C; 11A combined with example 10B or example 10C, 11A combined with example 11B or example 11C; 11A combined with example 12B or example 12C; 11A combined with example 13B or example 13C; 11A combined with example 14B or example 14C; 11A combined with example 15B or example 15C; 11A combined with example 16B or example 16C; 11A combined with example 17B or example 17C; 11A combined with example 18B or example 18C; 11A combined with example 19B or example 19C; 11A combined with example 20B or example 20C; 11A combined with example 21B or example 21C; 11A combined with example 22B or example 22C; 11A combined with example 23B or example 23C; 11A combined with example 24B or example 24C; 11A combined with example 25B or example 25C; 11A combined with example 26B or example 26C; 11A combined with example 27B or example 27C; 11A combined with example 28B or example 28C; 11A combined with example 29B or example 29C; 11A combined with example 30B or example 30C; 11A combined with example 31B or example 31C; 11A combined with example 32B or example 32C; 11A combined with example 33B or example 33C; 11A combined with example 34B or example 34C; 11A combined with example 35B or example 35C; 11A combined with example 36B or example 36C; 11A combined with example 37B or example 37C; 11A combined with example 38B or example 38C; 11A combined with example 39B or example 39C; 11A combined with example 40B or example 40C; 11A combined with example 41B or example 41C.

Furthermore, composition A and B that are contained within the kit-in-part according to the invention have constituents comprising examples Aa combined with examples B or C, equal to list I that describes the combination of A, B and C. Thus the following combinations of the above described examples are possible and given in list II: example 1Aa combined with example 1B or example 1C; example 1Aa combined with example 2B or example 2C; 1Aa combined with example 3B or example 3C; 1Aa combined with example 4B or example 4C; 1Aa combined with example 5B or example 5C; 1Aa combined with example 6B or example 6C; 1Aa combined with example 7B or example 7C; 1Aa combined with example 8B or example 8C; 1Aa combined with example 9B or example 9C; 1Aa combined with example 10B or example 10C; 1Aa combined with example 11B or example 11C; 1Aa combined with example 12B or example 12C; 1Aa combined with example 13B or example 13C; 1Aa combined with example 14B or example 14C; 1Aa combined with example 15B or example 15C; 1Aa combined with example 16B or example 16C; 1Aa combined with example 17B or example 17C; 1Aa combined with example 18B or example 18C; 1Aa combined with example 19B or example 19C; 1Aa combined with example 20B or example 20C; 1Aa combined with example 21B or example 21C; 1Aa combined with example 22B or example 22C; 1Aa combined with example 23B or example 23C; 1Aa combined with example 24B or example 24C; 1Aa combined with example 25B or example 25C; 1Aa combined with example 26B or example 26C; 1Aa combined with example 27B or example 27C; 1Aa combined with example 28B or example 28C; 1Aa combined with example 29B or example 29C; 1Aa combined with example 30B or example 30C; 1Aa combined with example 31B or example 31C; 1Aa combined with example 32B or example 32C; 1Aa combined with example 33B or example 33C; 1Aa combined with example 34B or example 34C; 1Aa combined with example 35B or example 35C; 1Aa combined with example 36B or example 36C; 1Aa combined with example 37B or example 37C; 1Aa combined with example 38B or example 38C; 1Aa combined with example 39B or example 39C; 1Aa combined with example 40B or example 40C; 1Aa combined with example 41B or example 41C.

The different combinations of composition A and composition B contained in the kit-in-part are given in list II and can be altered by exchanging 1Aa with one of the components selected from the group consisting of 2Aa, 3Aa, 4Aa, 5Aa, 6Aa, 7Aa, 8Aa, 9Aa, 10Aa, 11Aa, 12Aa, 13Aa, 14Aa, 15Aa, 16Aa, 17Aa, 18Aa, 19Aa, 20Aa, 21Aa, 22Aa, 23Aa, 24Aa, 25Aa, 26Aa, 27Aa, 28Aa, 29Aa, 30Aa, 31Aa, 32Aa, 33Aa, 34Aa, 35Aa, 36Aa, 37Aa, 38Aa, 39Aa, 40Aa, 41Aa, 42Aa, 43Aa, 44Aa, 45Aa, 46Aa, 47Aa, 48Aa, 49Aa, 50Aa, 51Aa, 52Aa, 53Aa, 54Aa, 55Aa and 56Aa.

According to a further aspect, the kit-in-part comprising any of the compositions A and B as defined above, preferably also comprises application devices and/or cleaning devices. The application devices contain cannula or syringes, preferably cannulas. The cleaning devices contain cotton bud, medical swabs, medical cotton gauzes or any other absorbant gauze, cotton wool, preferably cotton buds and/or medical cotton gauzes.

According to a further aspect, the kit-in-part comprises any of the compositions A and B as defined above, further comprises packaging material that preferably contains instructions for the use and dosage of said composition A and composition B that are contained within the kit-in-part. These instructions are added as an instruction leaflet or printed on the packaging material. Preferably, the instructions include the information about the use of composition A and composition B of the kit-in-part as described in the subsequent sections.

Composition A of the kit-in-part is used for the cleaning of the exterior part of the ear only. Thus, according to a further aspect, the kit-in-part provides composition A and composition B, wherein composition A enables the process of cleaning the exterior ear of an animal, preferably of a companion animal such as a cat or a dog. Preferably, composition A of the kit-in-part is any one of the cetrimide containing compositions described herein. The process of using the composition A of the kit-in-part for cleaning the exterior ear of an animal comprising preferably the steps: a) pouring composition A as described above into the auditory canal of the animal; b) letting composition A preferably react within the auditory canal of the animal; c) removing composition A from the auditory canal of the animal. In said process the ear is preferably massaged while the composition reacts. In the described process 1 to 50 ml are preferably used in step a). Furthermore, the process or more specifically the process steps a) to c) are preferably repeated.

According to a further aspect, the process of using composition A of the kit-in-part for the cleaning of the exterior of either healthy or inflamed ears is preferably performed in the following steps: a) composition A is poured into the auditory canal; b) then the ear is massaged; c) composition A will be removed, the ear will be cleaned and dried, preferably with cotton wool or with gauze. Preferably, the process steps a), b) and c) are repeated one or several times. The cleaning application is preferably repeated if one application was not sufficient. This cleaning process with composition A of the kit-in-part helps keeping chronic and/or chronic otitis externa of an animal, preferably companion animals such as a dog or a cat under control.

Composition B of the kit-in-part is used for treating the exterior part of the ear for diseases such as otitis externa. Otitis externa is caused by for example bacteria, parasites, foreign bodies or allergies. Preferably, composition B of the kit-in-part is any one of the corticosteroid, antibiotic and antifungal containing compositions described herein. The process of using composition B as defined above for the treatment of the exterior of inflamed ears is performed in the following steps: a) composition B is administered, preferably dropped, into the auditory canal; b) composition B reacts with the inflamed ear after administration. Preferably the ear is massaged while composition B reacts with the inflamed ear. The amount to be used depends on the size of the animal to be treated and comprises about 0.01 ml to 1 ml or 0.06 to 0.7 ml, preferably 0.1 to 0.5 ml, 0.1 to 0.4 ml, 0.1 to 0.3 ml, 0.2 to 0.3 ml, even more preferred are 0.1 to 0.3 ml, 0.2 to 0.3 ml per application. This equals about 2 to 20 drops per application, preferably 3 to 15, 3 to 12, 5 to 12, 3 to 10, 5 to 10, more preferred are 3 to 10 and 5 to 10. Generally, composition B of the kit-in-part will be applied 1 to 4 times per day, preferably 1 to 3 or 1 to 2 times per day, even more preferred twice daily. According to a further aspect, composition B of the kit-in-part is contained within a bottle with a volume of 5 to 50 ml, 5 to 40 ml, 5 to 30 ml, 5 to 20 ml or 15 ml, preferably 15 ml.

According to another aspect, the kit-in-part that comprises of composition A for the use of cleaning ears and composition B for treating ears of an animal, preferably a companion animal such as a dog or a cat and suitable packaging material, additionally comprises components selected from the group consisting of application and cleaning appliances/instruments such as preferably cannules, cotton swabs, gauzes, and information about the cleaning and treatment of ears of a said animal.

The composition A of the kit-in-part as described above is suitable for the use of cleaning ears and composition B of the kit-in-part as described above is suitable for the use of treating ears of an animal, preferably a companion animal, even more preferred dogs or cats. Thus, the present invention does not only relate to the kit-in-part as described hereinabove, it also relates to the use of said kit-in-part, in particular of composition A and composition B for cleaning and treating ears of an animal, preferably a companion animal such as a dog or a cat. Preferably, the above defined kit-in-part is used for cleaning and treating ears of an animal suffering from otitis externa. Otitis externa is caused by for example preferably bacteria, parasites, foreign bodies or allergies.

Thus, according to a further aspect, provided is a kit-in-part comprising any of the compositions A and B as defined hereinabove, preferably together with one of the application and cleaning appliances/instruments for the use of cleaning ears of an animal, preferably a companion animal, even more preferred a dog or cat. Preferably the cleaning includes the following process steps: a) pouring composition A as described above into the auditory canal of the animal; b) letting composition A preferably react within the auditory canal of the animal; c) removing composition A from the auditory canal of the animal. In said process the ear is preferably massaged while the composition reacts. In the described process 1 to 50 ml are preferably used in step a). Furthermore, the process or more specifically the process steps a) to c) are preferably repeated.

According to a further aspect, the cleaning step is done to clean inflamed ear prior to the medical treatment of said inflamed ear. It was found that cleaning an inflamed ear prior to the medical treatment with one or more anti-inflammatory agent, such as for example antibiotics, antiparasitics, antifungal and/or corticoids improves the effectiveness of such anti-inflammatory agent. Thus, according to a further aspect, the invention also relates to a kit-in-part comprising any of the compositions A and B as defined hereinabove, preferably together with one of the application and cleaning appliances/ instruments for the use of cleaning ears and for the use of treating an inflamed ear of an animal, preferably a companion animal, even more preferred a dog or cat. Preferably the cleaning of the inflamed ear includes the following process steps: a) pouring composition A as described above into the auditory canal of the animal; b) letting composition A preferably react within the auditory canal of the animal; c) removing composition A from the auditory canal of the animal. In said cleaning process the ear is preferably massaged while the composition A reacts. In the described process 1 to 50 ml are preferably used in step a). Furthermore, the process or more specifically the process steps a) to c) are preferably repeated. The treatment step preferably includes the following steps: a) composition B is administered, preferably dropped, into the auditory canal; b) composition B reacts with the inflamed ear after administration. Preferably the ear is massaged while composition B reacts with the inflamed ear. The amount to be used is the preferably the amount as defined hereinabove. Generally, composition B of the kit-in-part will be applied 1 to 4 times per day, preferably 1 to 3 or 1 to 2 times per day, even more preferred twice daily. According to a further aspect, composition B of the kit-in-part is contained within a bottle with a volume of 5 to 50 ml, 5 to 40 ml, 5 to 30 ml, 5 to 20 ml or 15 ml, preferably 15 ml. Preferably the cleaning of the inflamed ear as defined herein with any of the compositions A as described herein is done prior to the treatment of the inflamed ear as described above with any of the compositions B described herein.

It might not be necessary to clean the inflamed ear for each treatment with composition B. Thus, the kit-in-part, in particular composition B of said kit-in-part, can also be used to treat inflamed ears as such. Thus, according to a further aspect, the invention also relates to a kit-in-part comprising any of the compositions A and B as defined hereinabove, preferably together with one of the application and cleaning appliances/instruments for the use of treating an inflamed ear of an animal, preferably a companion animal, even more preferred a dog or cat. The treatment step preferably includes the following steps: a) composition B is administered, preferably dropped, into the auditory canal; b) composition B reacts with the inflamed ear after administration. Preferably the ear is massaged while composition B reacts with the inflamed ear. The amount to be used is the preferably the amount as defined hereinabove. Generally, composition B of the kit-in-part will be applied 1 to 4 times per day, preferably 1 to 3 or 1 to 2 times per day, even more preferred twice daily. According to a further aspect, composition B of the kit-in-part is contained within a bottle with a volume of 5 to 50 ml, 5 to 40 ml, 5 to 30 ml, 5 to 20 ml or 15 ml, preferably 15 ml. Preferably the cleaning of the inflamed ear as defined herein with any of the compositions A as described herein is done prior to the treatment of the inflamed ear as described above with any of the compositions B described herein.

The kit-in-part as described hereinabove for use of the treatment of inflamed ears, is preferably used for the treatment an animal that is suffering from otitis externa. Otitis externa can be caused by bacteria, parasites, foreign bodies or allergies. Thus, according to a further aspect, the invention also relates to a Kit-in-part comprising any of the compositions A and B as defined hereinabove, preferably together with one of the application and cleaning appliances/instruments for the use of treating an animal suffering from otitis externa, preferably caused by bacteria, parasites, foreign bodies or allergies. The treatment step preferably includes the following steps: a) composition B is administered, preferably dropped, into the auditory canal; b) composition B reacts with the inflamed ear after administration. Preferably the ear is massaged while composition B reacts with the inflamed ear. The amount to be used is the preferably the amount as defined hereinabove. Generally, composition B of the kit-in-part will be applied 1 to 4 times per day, preferably 1 to 3 or 1 to 2 times per day, even more preferred twice daily. According to a further aspect, composition B of the kit-in-part is contained within a bottle with a volume of 5 to 50 ml, 5 to 40 ml, 5 to 30 ml, 5 to 20 ml or 15 ml, preferably 15 ml. Preferably the cleaning of the inflamed ear as defined herein with any of the compositions A as described herein is done prior to the treatment of the inflamed ear as described above with any of the compositions B described herein.

A further aspect of the invention comprise a method of cleaning an inflamed ear of an animal, comprising cleaning the ear by a) pouring composition A of the kit-in-part as defined hereinabove into the auditory canal; b) letting said composition A react; c) removing said composition A. According to a further aspect, said method further comprises administering 5 to 50 ml of composition A is per application. Preferably, said animal is a companion animal, even more preferred a dog or cat. Preferably, said animal is suffering from otitis externa. Otitis externa is caused by for example preferably bacteria, parasites, foreign bodies or allergies.

A further aspect of the invention comprises a method of treating an inflamed ear of an animal, comprising treating the ear by a) administering, preferably dropping composition B into the auditory canal. Preferably the method comprises treating the ear by administering the composition B of the kit-in-part 1 to 4 times per day, preferably 1 to 3 or 1 to 2 times per day, even more preferred twice daily. According to a further aspect, said method further comprises administering 2 to 20 drops of composition B per administration, preferably 3 to 15, 3 to 12, 5 to 12, 3 to 10, 5 to 10, more preferred are 3 to 10 and 5 to 10 drops per administration. Preferably 1 drop includes about 0.03 ml of composition B. Preferably, said animal is a companion animal, even more preferred a dog or cat. Preferably, said animal is suffering from otitis externa. Otitis externa is caused by for example preferably bacteria, parasites, foreign bodies or allergies.

According to a further aspect, the invention relates to method of treating an inflamed ear of an animal comprising a) cleaning the inflamed ear with any of the compositions A described herein of the kit-in-part defined herein; and b) treating the inflamed ear with any of the compositions B as defined herein of the kit-in-part defined herein. Preferably the cleaning includes the following process steps: a) pouring the composition A as described above into the auditory canal of the animal; b) letting the composition A preferably react within the auditory canal of the animal; c) removing the composition A from the auditory canal of the animal. In said process the ear is preferably massaged while the composition reacts. In the described process 1 to 50 ml are preferably used in step a). Furthermore, the process or more specifically the process steps a) to c) are preferably repeated. The treatment step of the method described above preferably includes the following steps: a) composition B is administered, preferably dropped, into the auditory canal; and b) composition B reacts with the inflamed ear after administration. Preferably the ear is massaged while composition B reacts with the inflamed ear. The amount of composition B to be used is the preferably the amount as defined hereinabove. Generally, composition B of the kit-in-part will be administered 1 to 4 times per day, preferably 1 to 3 or 1 to 2 times per day, even more preferred twice daily. According to a further aspect, composition B of the kit-in-part is contained within a bottle with a volume of 5 to 50 ml, 5 to 40 ml, 5 to 30 ml, 5 to 20 ml or 15 ml, preferably 15 ml. Preferably cleaning of the inflamed ear as defined herein with any of the compositions A as described herein is done prior to the treatment of the inflamed ear as described above with any of the compositions B described herein. Preferably, said animal is a companion animal, even more preferred a dog or cat.

Preferably, the animal having an inflamed ear is suffering from otitis externa. Otitis externa is caused by for example preferably bacteria, parasites, foreign bodies or allergies. Thus according to a further aspect, the invention relates to a method of treating an animal, preferably a companion animal, even more preferred a dog or cat, suffering from otitis externa comprising a) cleaning the ear of said animal suffering from otitis externa with any of the compositions A described herein of the kit-in-part as defined herein; and b) treating the ear of said animal suffering from otitis externa with any of the compositions B as defined. The cleaning step and treatment step are preferably performed as described above for the method of treating an inflamed ear of an animal.

The invention claimed is:

1. A kit-in-part comprising compositions A and B that are separate from each other and are suitable for cleaning and treating ears of a companion animal, wherein composition A comprises cetrimide as antibacterial agent and one or more excipients selected from the group consisting of humectants and wetting agents, wherein composition B comprises sodium fusidate, framycetin sulphate, prednisolone and nystatin, and wherein composition A has a pH in the range of pH 4-9.

2. The kit-in-part according to claim 1, wherein the humectant is selected from the group consisting of glycerol, polyethylene glycol 200, polyethylene glycol 400, peanut oil, almond oil, olive oil, and sesame oil.

3. The kit-in-part according to claim 1, wherein composition B comprises an active pharmaceutical ingredient for treating ears.

4. The kit-in part according to claim 1, wherein composition A further comprises an aqueous solution of propylene glycol, glycerol and cetrimide.

5. The kit-in-part according to claim 3, wherein composition B comprises an active pharmaceutical ingredient selected from the group consisting of one or more antibiotics, one or more antifungal, one or more antiparasitics, one or more corticoids or combinations thereof.

6. The kit-in-part according to claim 1, wherein said kit further comprises application devices and/or cleaning devices, said application devices comprise a cannula or syringes and said cleaning devices comprise cotton swabs or medical cotton gauzes.

7. The kit-in-part according to claim 1, wherein said kit further comprises an information leaflet about the treatment of the infected and/or inflamed ear.

8. The kit-in-part according to claim 1, wherein composition A is suitable for cleaning inflamed or non-inflamed ears of an animal, including an exterior part of an ear of the animal.

9. The kit-in-part according to claim 1, wherein composition B is suitable for use of the treatment of inflamed ears of an animal, including an exterior part of an ear of the animal.

10. The kit-in-part according to claim 9, wherein said animal is suffering from otitis externa.

11. The kit-in-part according to claim 9, wherein the animal is a dog or a cat.

12. A method of cleaning an infected ear of a dog or a cat, comprising:
  a) pouring composition A of the kit-in-part defined in claim 1 into an auditory canal of the dog or the cat;
  b) letting composition A react within the auditory canal, wherein the ear of the dog or the cat is massaged while the composition reacts; and
  c) removing composition A from the auditory canal.

13. A method of treating an infected ear of a dog or a cat, comprising:
  a) administering composition B of the kit-in-part defined in claim 1 into an auditory canal of the dog or the cat.

14. The method according to claim 13, wherein composition B of the kit-in-part is administered 1 to 4 times per day.

15. A method of treating an inflamed or infected ear of a dog or a cat, comprising:
  a) cleaning the inflamed or infected ear with composition A of the kit-in-part as defined by claim 1; and
  b) treating the inflamed or infected ear with composition B of the kit-in-part as defined by claim 1.

16. The method according to claim 15, wherein the cleaning step a) comprises:
  i) pouring composition A into the auditory canal of the dog or the cat,
  ii) letting composition A react within the auditory canal, wherein the inflamed or infected ear of the dog or the cat is massaged by composition A reacts, and
  iii) removing composition A from the auditory canal.

17. The kit-in-part according to claim 1, wherein the wetting agent is selected from the group consisting of propylene glycol, 1,3-butandiol, ethanol, docusate sodium, and dimethyl sulfoxide (DMSO).

18. The kit-in-part according to claim 1, wherein composition A has a pH in the range of pH 5-8.

19. A kit-in-part comprising compositions A and B that are separate from each other and are suitable for cleaning and treating ears of a companion animal, wherein composition A comprises an aqueous solution of propylene glycol, glycerol and cetrimide, composition B comprises an active pharmaceutical ingredient for treating ears, wherein the active pharmaceutical ingredient consists of sodium fusidate, framycetin sulphate, prednisolone and nystatin, and the kit-in-part includes no other active pharmaceutical ingredient for treating ears, and wherein composition A has a pH in the range of pH 4-9.

* * * * *